United States Patent
Kindlein et al.

(10) Patent No.: US 7,252,629 B2
(45) Date of Patent: Aug. 7, 2007

(54) DEVICE FOR EFFECTING RADIATION THERAPY IN AN ANIMAL BODY

(75) Inventors: Johann Kindlein, Oberhausen (DE); Dennis Robert Schaart, Delf (NL)

(73) Assignee: Nucletron B.V., Veenedaall (NL)

( * ) Notice: Subject to any disclaimer, the term of this patent is extended or adjusted under 35 U.S.C. 154(b) by 323 days.

(21) Appl. No.: 10/301,682

(22) Filed: Nov. 22, 2002

(65) Prior Publication Data
US 2003/0128808 A1    Jul. 10, 2003

(30) Foreign Application Priority Data
Nov. 23, 2001  (EP) .................. 01204554

(51) Int. Cl.
*A61N 5/00*  (2006.01)
(52) U.S. Cl. ............................................ 600/3
(58) Field of Classification Search ............ 600/1–8
See application file for complete search history.

(56) References Cited

U.S. PATENT DOCUMENTS

| | | | |
|---|---|---|---|
| 4,631,415 A * | 12/1986 | Sauerwein et al. ...... 250/497.1 |
| 5,344,383 A * | 9/1994 | Liping ........................ 600/3 |
| 5,428,658 A | 6/1995 | Oettinger et al. | |
| 5,729,583 A * | 3/1998 | Tang et al. .................. 378/122 |
| 6,048,300 A * | 4/2000 | Thornton et al. ............... 600/7 |
| 6,132,423 A | 10/2000 | Aita et al. | |
| 6,554,824 B2 * | 4/2003 | Davenport et al. ............. 606/3 |
| 2003/0149330 A1 * | 8/2003 | Geitz ........................... 600/3 |

FOREIGN PATENT DOCUMENTS

| | | |
|---|---|---|
| EP | 0 523 417 A1 | 1/1993 |
| EP | 1 057 500 A1 | 6/2000 |
| WO | WO 99/44687 A1 | 9/1999 |
| WO | WO 99/66988 A1 | 12/1999 |

\* cited by examiner

*Primary Examiner*—John P. Lacyk
(74) *Attorney, Agent, or Firm*—Birch, Stewart, Kolasch & Birch, LLP

(57) ABSTRACT

A device for effecting radiation therapy in an animal body has a housing provided with at least one outlet channel, a guide tube connected at one end with the outlet channel and wherein the other end of the guide tube is positionable in the animal body near the site of the intended radiation therapy, one electro-magnetic radiation emitting source connected to a first end of a transport wire, and a transport device for moving the transport wire and the radiation emitting source via the outlet channel through the guide tube to and from the site of the intended radiation therapy in the body. The transport device has a rotatable drum, which is rotationally symmetric around a rotation axis. The drum is provided with two end surfaces, and a circumferential surface is provided with at least one winding groove for at least one transport wire.

30 Claims, 6 Drawing Sheets

DEVICE FOR EFFECTING RADIATION THERAPY IN AN ANIMAL BODY

This nonprovisional application claims priority under 35 U.S.C. § 119 (a) on Patent Application No. 01204521.8 filed in EUROPE on Nov. 23, 2001, which is herein incorporated by reference.

The invention relates to a device for effecting radiation therapy in an animal body comprising a housing provided with at least one outlet channel, a guide tube connected at one end with said outlet channel and wherein the other end of said guide tube is positionable in said animal body near the site of the intended radiation therapy, one electromagnetic radiation emitting source connected to a first end of a transport wire, and transport means for moving said transport wire and said radiation emitting source via said outlet channel through said guide tube to and from said site of the intended radiation therapy in said body.

DESCRIPTION OF THE BACKGROUND ART

It is known in the medical field to use afterloader devices in the treatment of cancerous tumours using radioactive sources having intensity greater than that which can safely be handled. Remote afterloaders are devices generally used in the cancer treatment field to accurately advance and retract a flexible wire containing an electro-magnetic radiation emitting source over a specified distance for a specific time period. A remote afterloader comprises a flexible simulation wire for testing purposes and a flexible wire with the electro-magnetic radiation emitting source, controllers and transport mechanisms to operate both types of wires, as well as a radiation shielded housing for the radiation emitting source.

Typically one or more catheters, needles, or other closed pathways (hereafter "guide tubes") to the treatment site are positioned in the patient. The guide tubes are then attached to the afterloader, which advances the radioactive source at the end of the transport wire, sometimes called a source-wire, along the guide tubes according to a predetermined sequence calculated to deliver a therapeutic dose of radiation to the tumour. Many of these prior art devices advance the source-wire by means of a friction drive belt trained about a wheel with the wire sandwiched between the belt and wheel.

The radiation emitting sources presently used are radioactive sources, e.g. in the form of implant seeds or in the form of radioactive sources which are inserted through a hollow guide tube towards the site of intended therapy by means of a transport wire, which sources continuously emit electro-magnetic radiation following the principles of natural radioactive decay and which are characterized by the specific half life time of the used radioactive material. Since the sources used in such treatment can constitute a hazard to a technician administering the treatment, afterloaders are used for inserting of the radioactive source and the treatment therewith in the patient with minimum radiation exposure of the technician or with no exposure whatsoever.

For minimising the exposure of radioactive radiation to the environment these afterloader devices require a heavily constructed and expensive radiation shielded housing. The known afterloader devices allow the insertion of the radioactive source in the patient after the technician administering the treatment moves away from the patient or leaves the treatment room. In other words, the radioactive source is loaded into the patient for treatment after the technician leaves the patient, and for that reason such devices are generally referred to as "afterloading devices".

The effective treatment with a discreet radioactive source is dependent upon the particular tumour, the position of the tumour in the body, the activity of the source and the accuracy of positioning the source near or in the tumour. Such treatments involve an intrusion into the animal body, e.g. human body, and that intrusion may be through a natural orifice in the body, such as a blood vessel or lung trachea, if the tumour so admits, or by way of implanting flexible or rigid needles and other special devices in or near the tumour.

In either case, the effectiveness of the radiation treatment depends on accurately placing the radiation emitting source at the correct position near the tumour. With some tumours, a single radioactive source may be sufficient for effective treatment, but with other tumours, multiple sources, positioned in and around the tumour, may be required. In addition, with such multiple positioning of radioactive sources, the amount of radiation for effective treatment may vary with the different positioned sources, and therefore, specific regimens of treatment are often necessary in terms of both the positioning of the radiation emitting source and the duration of radiation exposure of the tumour.

Generally speaking, the radioactive sources used with these afterloading devices fall into two categories. The first category is that of a low dose rate (LDR) source, and the second category is that of a high dose rate (HDR) source. An LDR source emits low levels of radiation and can be safely handled by a technician for short periods of time. An HDR source emits high doses of radiation and cannot be safely handled by a technician, even for relative short periods of time. The after-loading devices for handling these two different radioactive sources are thus divided into two categories of machines, i.e. a low dose rate (LDR) machine and a high dose rate (HDR) machine.

An example of an afterloading device as described in the introduction is for example disclosed in U.S. Pat. No. 5,030,194. In that device a flexible wire is driven by suitable transport means together with a LDR or HDR source attached to one end from an outlet channel present a radiation shielded block or housing, through a guide tube and to the site of intended therapy in the patient by means of an applicator, e.g. an implant needle or catheter. Said applicator is positioned by a physician into the patient's body prior to the insertion of the radioactive source. The positioning of the needle or catheter into the body is sometime performed surgically and the correct position of that applicator near the site of the intended therapy is determined using suitable imaging techniques, like X-ray or ultrasound imaging means.

Effective treatment with a LDR source may often span many hours, e.g. 20 or 30 or even 50 hours. During such extended treatment, the patient can carry out normal body functions and the LDR source will likewise move in relation to the tumour. It is assumed that such movements will average out the radiation around the tumour and, therefore, a very accurate positioning of the LDR source, opposite the tumour, is not necessary.

However, the above assumptions are not always correct and incorrect positioned LDR sources may result. This results in less effective or ineffective therapy and, in addition, may unnecessarily expose healthy tissue to radiation. Thus, this procedure is less than desirable. In addition, it is often necessary to employ multiple LDR sources at different sites around the general site of intended therapy, even when treating a single localized tumour, since a single LDR source does not emit sufficient radiation to effectively treat many, even localized, tumours. In such case, the same procedure described above is used for each different site of intended therapy and the above-noted inaccuracies will affect the effectiveness of the radiation therapy.

With high dose rate (HDR) devices, the HDR source is too radioactive for operation in the manner of the LDR device. However the desired accuracy of the present HDR devices are even more hard to achieve, since exposure of the tumour to the high dose radiation is often only in terms of minutes, e.g. 10, 15 or 20 minutes, and a small inaccuracy in positioning the HDR source can result in large inaccuracies in effective treatment, in view of the short times involved.

Besides the negative effects relating to an inaccurate positioning of the radioactive source in the body and the undesired exposure to radioactive radiation of the technician the natural radioactive decay of the radioactive sources now used require a proper analysis of the decay state of the radioactive source before insertion into the body near the site of the intended therapy. This in order to obtain a correct calculation of the time, intensity and amount of the radiation emitted. However due to the natural radioactive decay of the radioactive source during time the actual radiation intensity and amount emitted during the treatment inside the patient body can differ (read: can be less) from the necessary radiation exposure (time and intensity) as planned prior to the treatment using suitable dosimetric therapy planning software.

BRIEF SUMMARY OF THE INVENTION

It is an object of the invention to provide a device for effecting radiation therapy in an animal body using a radiation emitting source according to the above technique, wherein a) a radiation emitting source is used for applying emitted radiation corresponding more accurately to the preplanned and desired amount, intensity and duration to the site of the intended therapy, which b) is both applicable for LDR and HDR treatments and wherein c) undesired exposure to radiation of the medical personnel and/or technicians administering the radiation therapy completely is avoided.

According to the invention the device is characterized in that said radiation emitting source is an activatable radiation emitting source, which is operative between an activated and un-activated state. Thus not only undesired exposure is avoided resulting in a more safe device for its environment, which device no longer requires a radiation shielded housing making the device cheaper to construct with minimised dimensions. Moreover the amount, intensity and duration of the radiation emitted can be applied more accurate, which radiation will more perfectly match the desired amount of radiation to be dosed as preplanned prior to the actual therapy. Furthermore said activatable radiation emitting source is applicable for both LDR and HDR applications. Therefore only one afterloading device can be used for both different administering applications, which significantly make the device according to the invention more versatile.

In order to more accurately apply a desired amount of radiation to the site of the intended therapy the device according to the invention is further characterized in that in activated state the amount, intensity, and/or duration of the radiation emitted by said activatable radiation emitting source is controllable and/or adjustable, wherein preferably said radiation emitting device is an X-ray device.

Especially the use of an activated X-ray device as a radiation emitting source has proven to be very suitable for use in afterloading radiation therapy, which X-ray device is furthermore very accurate and easy to control.

Another very effective embodiment according to the invention is characterized in that said activatable radiation emitting source is the tip of an optical fibre contained in said transport wire emitting laser light.

Preferably said activatable radiation emitting source is powered by a power supply placed outside the body, which power supply is preferably controllable. Therefore the activatable radiation emitting source can emit a preplanned desired amount of radiation with a specific amount, intensity and duration to a tumour in the patients body.

In a specific embodiment of the device according to the invention said transport wire comprises a power supply line for connecting said activatable radiation emitting source with the power supply, wherein preferably said power supply line is an optical fibre and said power supply is a laser device. Furthermore said power supply line comprises an electric supply line and said power supply comprises a high voltage power supply.

By only using an optical fibre of which the tip serves as radiation emitting source and a laser device as power supply, this embodiment of the device according to the invention can be used for photodynamic treatment of all kinds of cancerous tumours.

A further embodiment of the device according to the invention is characterized in that said device comprises an indexer provided with a plurality of outlet channels to which a plurality of said guide tubes are connected. More specifically said indexer is provided with means for directing at least said activatable radiation emitting device through at least one of said plurality of outlet channels, wherein said means comprise a guide block provided with at least one bore, which block is movably connected to the indexer, and wherein said at least one bore can be brought into alignment with at least one of said plurality of outlet channels.

With this embodiment it is possible to move the activatable radiation emitting source in un-activated state through one of said guide tubes to a site in or near a tumour to be treated at which position the radiation emitting source can be activated, thereby emitting a desired amount of radiation with a certain intensity and duration. Then said radiation device can be retracted from said guide tube in an un-activated state, and by means of said guide block and said indexer inserted in another of said plurality of outlet channels and guided through another guide tube towards another site near or in the tumour to be treated. Hence the radiation emitting source is activated when the source is in the position where the radiation should be deposed and deactivated when the treatment time ends.

Thus it is possible to position the same activatable radiation emitting source at different locations in or near the site of intended treatment, wherein the radiation emitting source at each site is activated for emitting a desired dose of radiation with a specific intensity and duration. This provides a multiple position radiation treatment with one and the same radiation emitting source.

With an embodiment where more than one radiation emitting sources are used for simultaneously applying a specific amount of radiation at different positions near or in a tumour in a patients body, the device is according to the invention characterized in that said guide block is provided with a row of a plurality of bores, which row can be brought in alignment with a row of a plurality of said outlet channels.

More especially according to another embodiment said transport means comprise a rotatable drum, which is rotationally symmetric around a rotation axis, which drum is provided with two end surfaces and a circumferential surface provided with at least one winding groove for at least one transport wire, wherein furthermore said drum can be at least partly hollow.

A compact construction of the device according to the invention can be obtained by mounting said power supply at an end surface of said drum or by mounting said power supply inside said drum.

A further reduction in components can be obtained in one specific embodiment by using one single power supply connected to a plurality of power supply lines.

In an embodiment of the device according to the invention wherein a laser device is used as power supply the device is characterized in that the laser device is connected to said plurality of optical fibre power supply lines by means of a beam splitter.

Another advantage of the use of radiation emitting source which is operative between an activated and un-activated state is that in the un-activated state said activatable radiation emitting source is used as a test source for testing the implantation through at least one guide tube towards a site of the intended radiation therapy in said body.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will now be become more fully understood from the detailed description given hereinbelow and the accompanying drawings, which are given by way of illustration only, and thus are not limitative of the present invention, and wherein:

FIG. 3b enlarged view of the embodiment as disclosed in FIG. 3a;

DETAILED DESCRIPTION OF THE INVENTION

Figure 1:
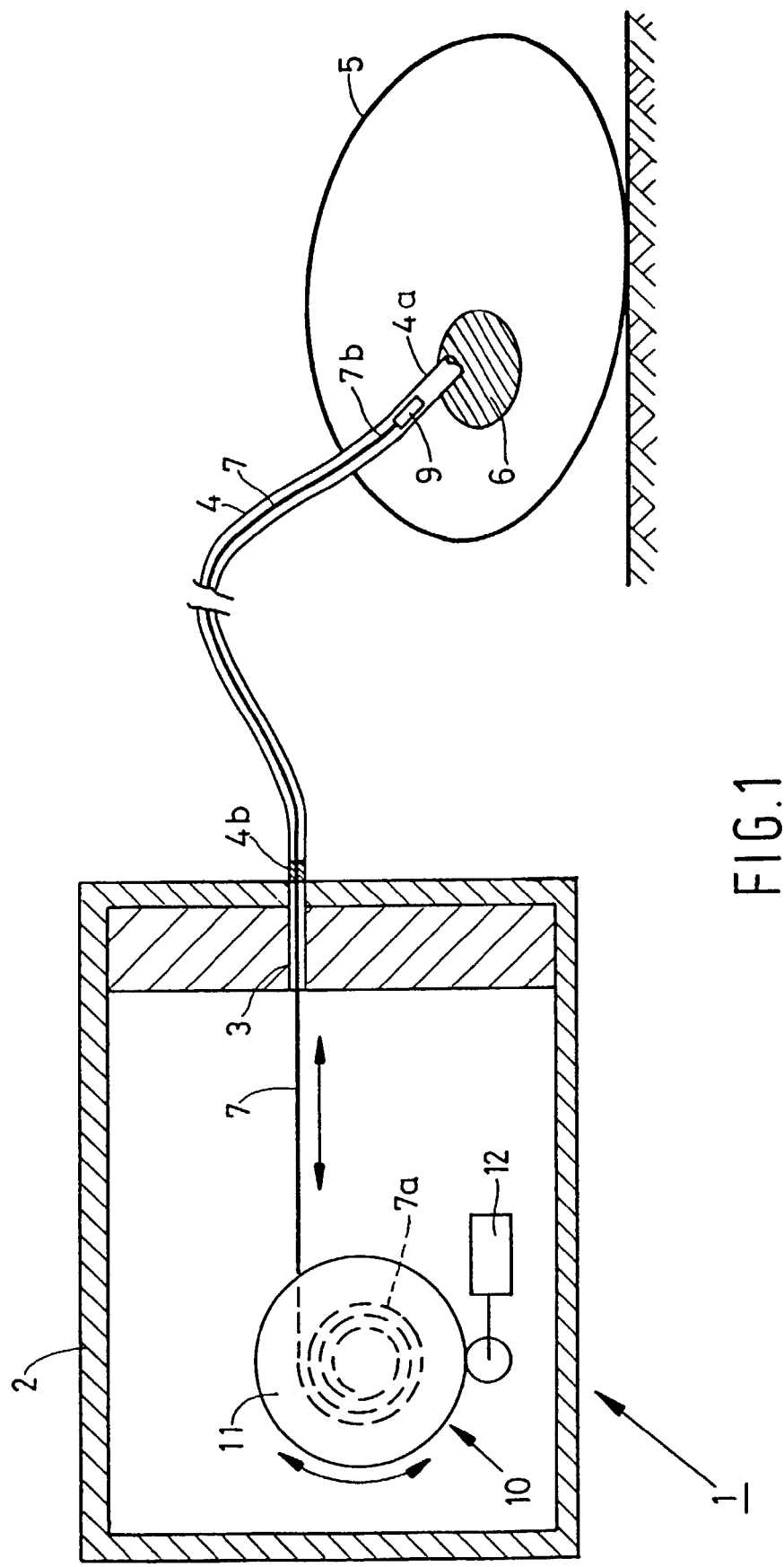
FIG. 1 an afterloading device according to the state of the art.

In FIG. 1 a device for effecting radiation therapy in an animal body according to the state of the art is disclosed, which device herein is referred to as an afterloading device as described in the introduction.

Said afterloading device 1 comprises a radiation shielded housing 2 wherein an outlet channel 3 is provided. Furthermore in said housing transport means 10 are present, which functionality will be explained later. In order to administer a radiation emitting source at a desired site of intended radiation therapy, for example in or near a tumour 6 present in an animal body 5 a guide, mostly flexible tube 4 like a catheter is implanted surgically or by means of an intrusion through a natural orifice in the body, such as blood vessel or lung trachea. The guide tube is with one end 4b connected to said outlet channel 3 and with its other end 4a placed in or near the tumour 6. Another technique for implanting the flexible catheter 4 is the use of a rigid hollow needle 4a, which can be implanted in or near the tumour or malignancy in said animal body 5.

Said radiation emitting source 9 is inserted into said animal body by means of a transport wire 7, which is contained by transport means 11, wherein the transport wire has an end 7a connected to said transport means 10 and which wire is with its other end 7b connected with said radiation emitting source.

Once the guide tube 4 is implanted at the desired location in said animal body 5 the insertion of the radiation emitting source is first tested by implanting a so called test source with a test wire through said guide tube 4 until the desired location in said body 5 near the tumour to be treated by radiation therapy has been reached. For testing purposes the afterloading device 1 is provided with a second test unit (not shown) comprising similar transport means 10, a similar test wire 7, which test wire 7 can be moved through the outlet channel 3 through the guide tube 4 towards the tumour 6 prior to the insertion of the actual transport wire 7 with the radiation emitting source 9.

As mentioned in the introduction of this application the radiation emitting source 9 is a radio-active source, emitting radiation following the principles of natural decay. Although the device 1 has a proper radiation shielded housing 2 for shielding the environment against radiation emitted by said radioactive source 9, when said source 9 is in its initial position inside the housing 2 prior to the insertion through the guide tube 4 into the body 5, the environment will be exposed to radioactive radiation once the radioactive source 9 has left the housing 2 through the outlet channel 3 and is advanced by the transport means 10 and the transport wire 7 through the guide tube 4 towards the site of the intended radioactive therapy.

According to the invention a radioactive source 9 as used in the afterloading device according to the state of the art is replaced by an activatable radiation emitting source, which is operative between an activated and un-activated state.

Said activatable radiation emitting source, which is preferably an X-ray emitting source, is activated once it is properly positioned near or in the tumour 6 to be treated, thereby reducing the exposure to radiation of the environment, for example persons who are administering the radiation therapy to the patient. Furthermore with the use of an activatable radiation emitting source the radiation administered to the tumour 6 can be well controlled, and especially the amount of radiation as well as its intensity and duration can be well controlled and can match the amount, intensity and duration of the desired radiation as preplanned by suitable dosimetric therapy planning software. Moreover a simplified, cheaper construction with minimised dimensions is obtained whilst a heavy, expensive radiation shielded housing is no longer required.

Preferably the activatable radiation emitting source is an X-ray emitting source, which at the amount, the intensity and the duration of the radiation emitted can be controlled and or adjusted by suitable control means. This makes the afterloading device according to the invention suitable for both LDR treatments as well as HDR treatments.

Figure 2A:
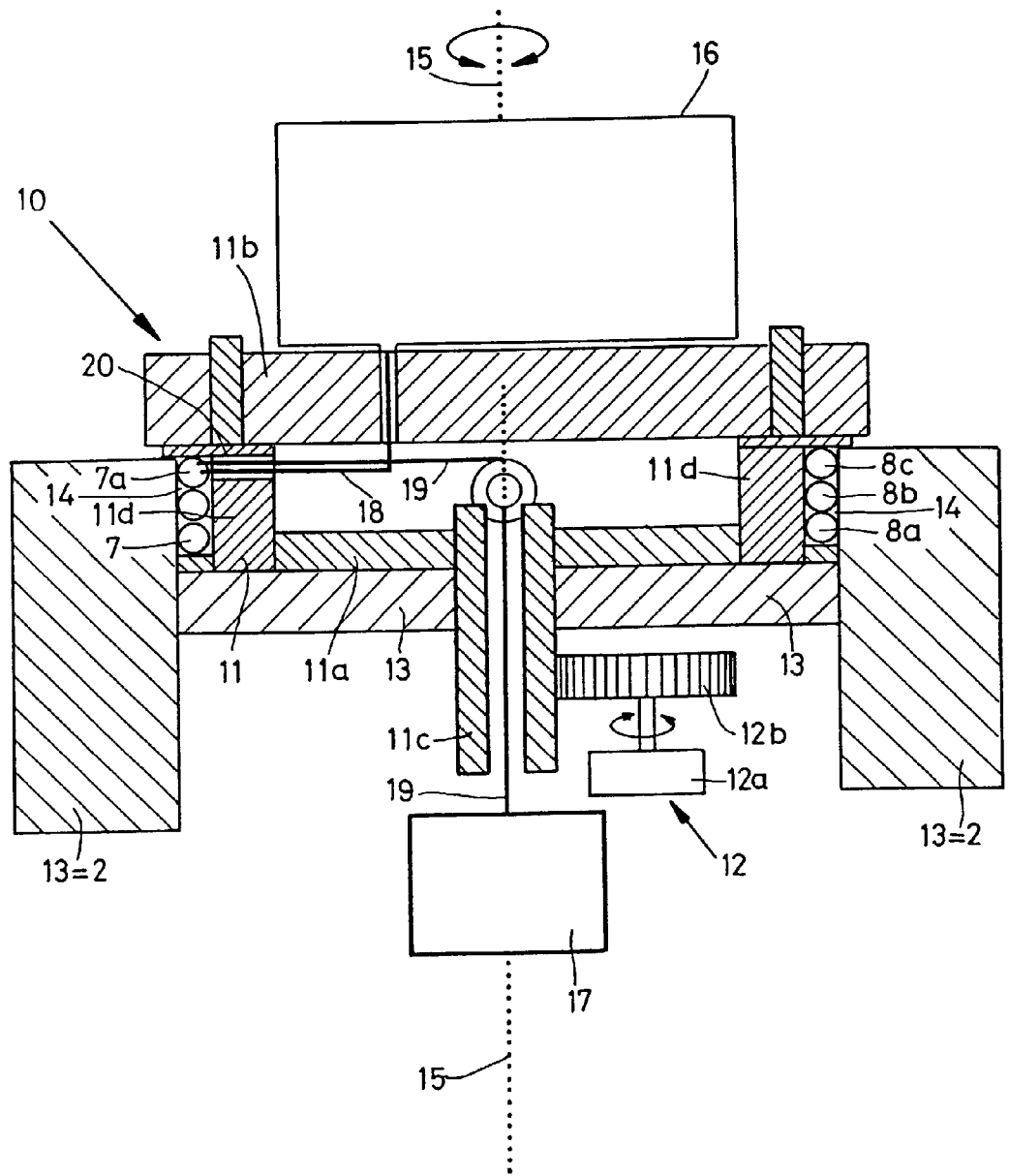
FIG. 2a an embodiment of the transport means for use in an afterloading device according to the invention.

In FIG. 2a a specific embodiment of the afterloading device according to the invention is disclosed, showing specific transport means 10 for advancing a transport wire 7 together with the activatable radiation emitting source 9 (not shown) through the guide tube 4 (also not shown) towards the site of intended therapy (also not shown). The activatable radiation emitting source 9 requires a power supply line which is incorporated in the transport wire 7. Preferably the radiation activated source is an X-ray emitting source, which is powered in one embodiment by a high voltage power supply 17.

The high voltage power supply 17 can be used for creating free electrons from a suitable filament, which electrons are accelerated by a suitable electrical field potential applied by said high voltage power supply. In another embodiment the high voltage power supply 17 is only used for accelerating the electrons, which are freed by means of the photoelectric effect or by means of the filament through which a current from another electric source is applied. In every situation, said accelerated electrons impinge on the anode for creating an X-ray beam which leaves the X-ray source via an aperture.

With another embodiment a laser device 16 is also part of the power supply for creating free electrons by means of the photoelectric effect. Said free electrons are then accelerated by the electric field potential for creating X-ray radiation.

Both high voltage supply 17 and laser device 16 are therefore connected with suitable power supply lines 19 and 18, which are incorporated inside the transport wire 7 and connected with the X-ray emitting source 9 positioned at the other end 7b of the transport wire 7.

The transport means 10 comprise a drum 11 which is rotatable about rotational axis 15 by means of suitable drive means 12, comprising a motor 12a and a rotational wheel 12b provided with a mesh, which cooperates with a corresponding mesh provided on the central shaft 11c of the drum 11.

In this embodiment the high voltage power supply 17 is positioned in the line of the central axis 15 of the drum 11 and the high voltage power supply line 19 is placed along the central axis 15 towards the interior of the drum 11, where it enters the transport wire 7 through an orifice 20 present in the circumferential surface of the drum 11, to which the end 7a of the transport wire 7 is connected. Furthermore the laser device 16 is connected to an end plate 11b of the drum 11 and the supply line 18, being an optical fibre 18 enters the transport wire 7 through the same orifice 20. Both supply lines 18 and 19 are contained in the transport wire 7 and are connected with the X-ray device 9 (not shown) connected to the other end 7b of the transport guide 7 (also not shown).

The whole construction comprising the drum 11 connected via end plate 11a with the rotation shaft 11c together with the laser device 16 is rotationally driven by the drive means 12 around the axis 15. With reference number 13 the solid earth is depicted, corresponding to the housing 2 of the device 1.

When rotating the drum 11 together with the laser device 16 by means of the drive means 12 transport wire 7 is unwound and advanced together with the X-ray emitting source 9 through the outlet channel 3 and the guide tube 4 towards the site of intended therapy in or near the tumour 6 (see FIG. 1). In the embodiment shown in FIG. 2a the drum 11 is provided with a groove 14 present in the circumferential surface of the drum 11 in which groove 14 the transport wire 7 is accomodated in several windings 8a, 8b, 8c. When rotating the drum 11 the transport wire 7 is unwound, whereby the whole construction including the laser device 16 rotates around the axes 15. The high voltage power supply 17 is thereby not rotated.

With this construction of the transport means 10 a very compact device can be obtained allowing a very accurate positioning of the X-ray emitting source 9 into the body 5.

Laser device 16 and high voltage power supply 17 are driven and controlled by suitable known means (not shown) allowing to activate the radiation X-ray emitting source 9 in such a manner that the X-ray beam radiated by the X-ray emitting source 9 is well controlled and can be adjusted according to the intended or preplanned radiation therapy. This means that the amount, the intensity and the duration of the X-ray beam emitted by the X-ray emitting source 9 can be very accurately controlled, resulting in a therapy treatment which matches very accurately the intended treatment as preplanned by suitable dosimetric therapy planning software.

Furthermore undesired exposure to radiation of the environment (including medical personal and/or technicians) is hereby completely avoided. Furthermore due to the absence of radioactive sources, which emit radiation following the principles of natural decay no radiation is exposed during the advancement of the source 9 through the guide tube 4 prior to its positioning at the site of intended therapy in the tumour 6.

Figure 2B:
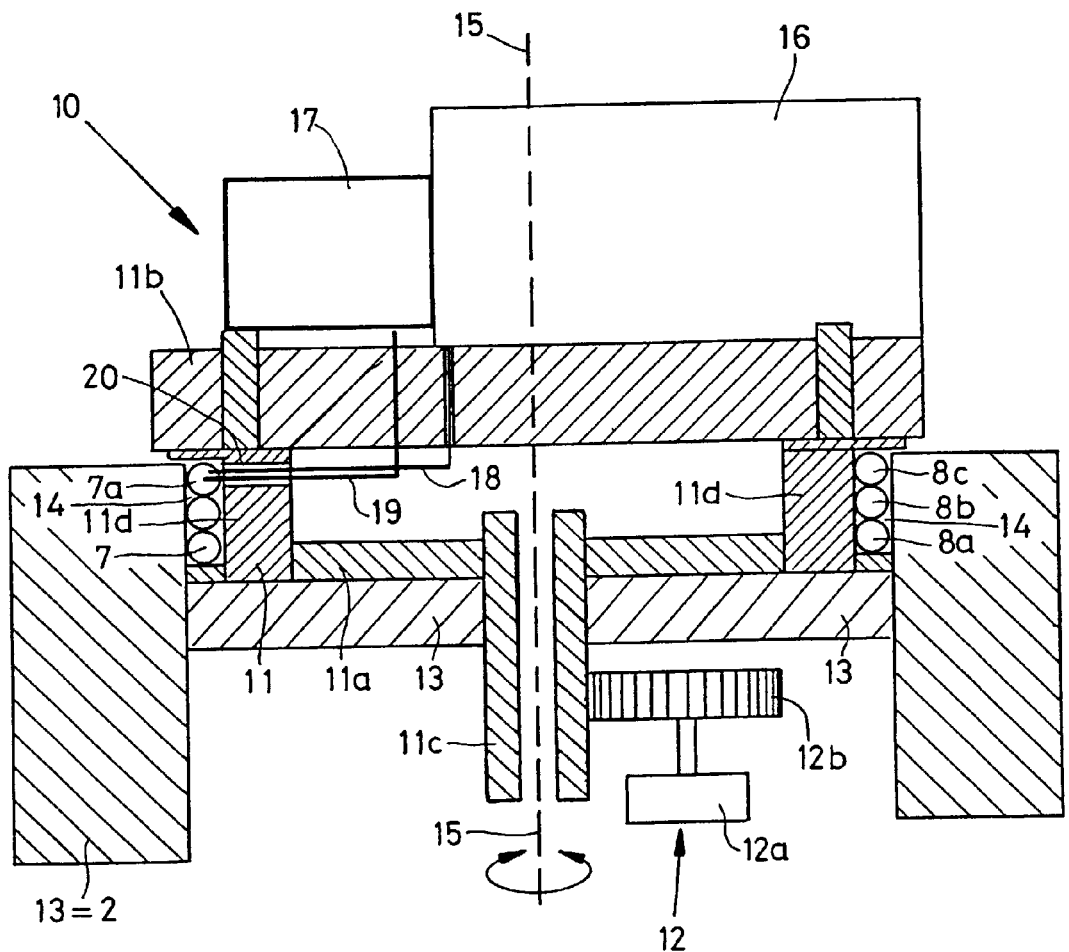
FIG. 2b another embodiment of said transport means for use in an afterloading device according to the invention.

In FIG. 2b a more compact construction of the transport means 10 according to the invention is disclosed, wherein corresponding parts are depicted by the same reference numerals. In this more compact embodiment also the high voltage power supply 17 is mounted on the rotational end plate 11b of the drum 11.

Figure 3A:
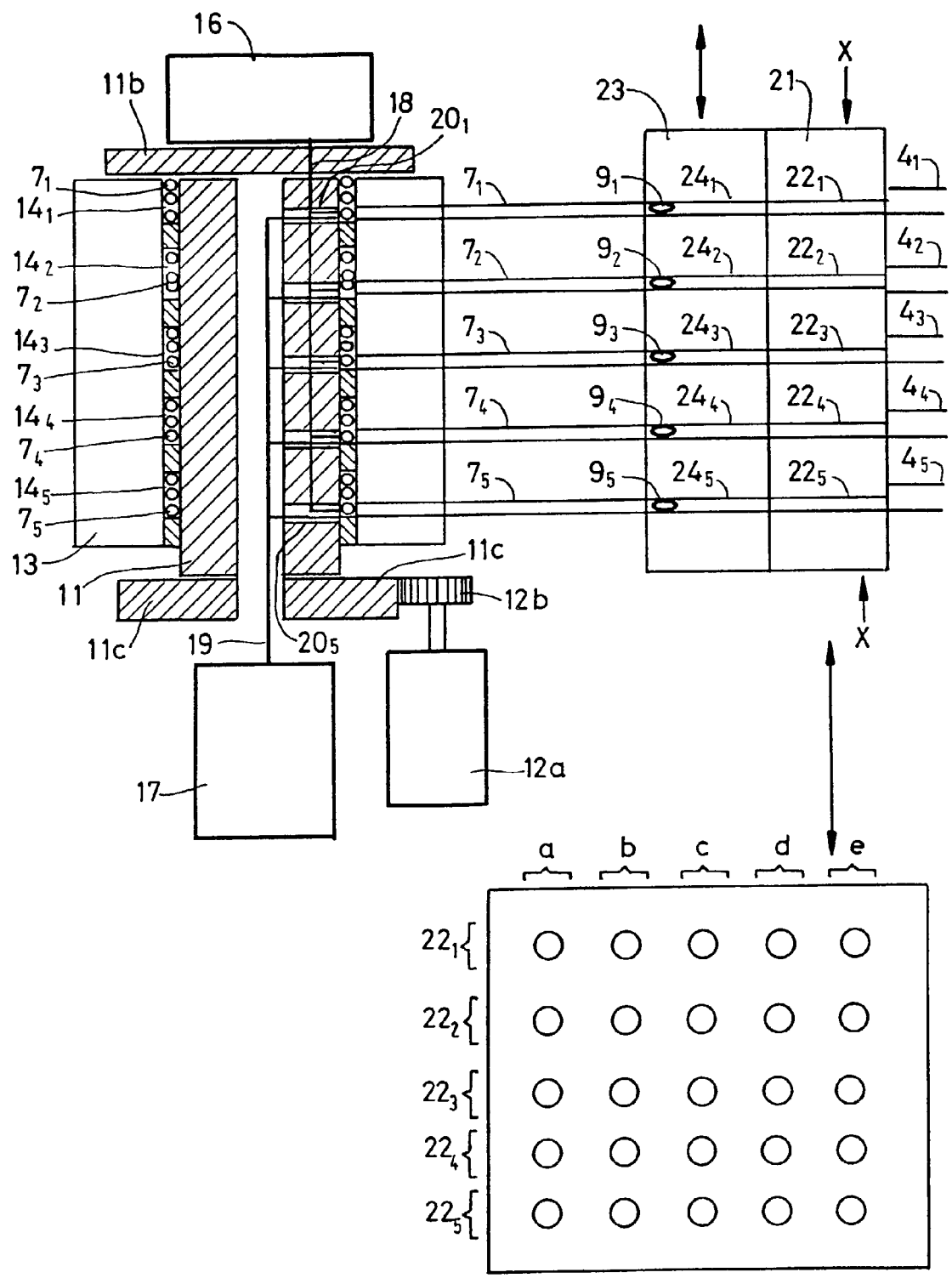
FIG. 3a a further embodiment of transport means for use in a multiple insertion of radiation emitting sources in an afterloading device according to the invention.

Another embodiment, almost similar to the embodiment of the transport means 10 as shown in FIG. 2a is depicted in FIG. 3a, wherein the afterloading device according to the invention is furthermore provided with an indexer 21 provided with a plurality of outlet channels $22_1$-$22_5$, to which outlet channels a plurality of guide tubes $4_1$-$4_5$ are connected.

Furthermore the rotational drum 11 is provided with a plurality of grooves $14_1$-$14_5$ present in the circumferential surface of the drum 11, in which grooves several transport wires $7_1$-$7_5$ are located. Each separate transport wire $7_1$-$7_5$ is provided on its end 7b (not shown) with an activatable radiation emitting source, preferably an X-ray radiation emitting source $9_1$-$9_5$ (not shown). The drum 11 is for each transport wire $7_1$-$7_5$ provided with grooves $14_1$-$14_5$ and orifices $20_1$-$20_5$ through which the power supply line 18 from the laser device 16 and the power supply line 19 of the high voltage power supply 17 are guided and which are accommodated in each transport wire.

In this embodiment simultaneously five transport wires $7_1$-$7_5$ and X-ray emitting sources $9_1$-$9_5$ associated with these wires can be inserted through similar guide tubes $4_1$-$4_5$ to five different locations in or near the tumour 6 (see FIG. 1). By means of different power supply lines 19 connected to the high voltage power supply 17 the different radiation X-ray emitting sources $9_1$-$9_5$ can be differently controlled, which means that the radiation (intensity, amount, duration) emitted by each X-ray emitting source $9_1$-$9_5$ can be controlled and adjusted separately depending on the intended, preplanned radiation therapy.

Although the indexer 21 can be provided with five separate outlet channels $22_1$-$22_5$ for passing five separated transport wires $7_1$-$7_5$ with five X-ray emitting sources $9_1$-$9_5$ associated therewith, it is also possible to use an indexer 21 wherein the outlet channels $22_1$-$22_5$ are arranged in a plurality of rows a, b, c . . . etc. An example of the indexer 21 is disclosed in the detailed view X-X in FIG. 3a, wherein the indexer 21 comprises a matrix of 5×5 outlet channels, arranged in five columns a-e and five rows $22_1$-$22_5$.

With this embodiment of the indexer 21 as shown in detail X-X five transport wires $7_1$-$7_5$ can be advanced simultaneously through five outlet channels $22_1$-$22_5$ of for example column a. Twentyfive guide tubes $4_1$-$4_{25}$ are connected with the several outlet channels $22_1$-$22_{25}$ and implanted at 25 different locations in or near the tumour 6 to be treated. After emitting a certain preplanned amount of radiation at the five positions in the tumour 6 associated with the guide tubes connected with the five outlet channels in column a the respective five X-ray emitting sources $9_1$-$9_5$ are de-activated, retracted in de-activated state together with their transport wires $7_1$-$7_5$ in backwards direction by rotating the drum 11 in a winding direction with the motor drive means 12, until the separate X-ray emitting sources $9_1$-$9_5$ are present in bores $24_1$-$24_5$ of guide block 23, which is moveably mounted with the indexer 21.

The guide block 23 can be moved with respect to the fixed indexer 21 by suitable means (not shown) such that the bores $24_1$-$24_5$ can be brought in alignment with another column a-e of outlet channels $22_1$-$22_5$, for example with the outlet channels present in column b as shown in the detailed view X-X. By driving the drum 11 in an unwinding direction the transport wires $7_1$-$7_5$, which were retracted after the first radiation session from the first five therapy-locations are now advanced together with the X-ray emitting sources $9_1$-$9_5$ through the guide tubes 4 connected with the outlet channels $22_1$-$22_5$ of column b of the indexer 21 towards five new different positions in the tumour 6 to be treated.

Once again the X-ray emitting sources $9_1$-$9_5$ are activated by the laser device 16 and the high voltage power supply 17 each emitting X-ray radiation with a—for each X-ray emitting source 9—specific amount, intensity, duration and direction. Once the radiation session in these new five locations is terminated, the X-ray emitting sources $9_1$-$9_5$ are then de-activated, retracted to their initial position in the bores $24_1$-$24_5$ of the guide block 23 inside the housing 2 of the afterloading device 1 by means of the motor means 12, which now drive the drum 11 in a winding direction. Once the X-ray emitting sources $9_1$-$9_5$ are fully retracted back into the housing 2, guide block 23 can be further advanced to an other column, for example column c, for a further radiation treatment with the X-ray emitting sources $9_1$-$9_5$ at five another locations.

With the afterloading device according to the invention the same radiation X-ray emitting source 9 can be used in a sequential order, to emit X-ray radiation at different locations in a tumour, wherein at each location the amount, intensity and duration of the applied radiation can be controlled or adjusted according to the preplanned intended and desired therapy treatment. During its advancement towards the position of intended radiation therapy and backwards towards the bores 24 inside the guide block 23 after radiation treatment the X-ray emitting source 9 is de-activated. This prevents any undesired and hazardous exposure of radiation to the environment, whilst each radiation emitting source 9 is only activated once said source is properly positioned near or inside the tumour 6.

Although in FIG. 3a an indexer 21 is used containing a matrix of 5×5 outlet channels 22, wherein during one session five X-ray emitting sources $9_1$-$9_5$ are advanced simultaneously through five guide tubes 4 and radiation therapy can be performed at five different locations inside an animal body, it shall be clear for the skilled man to use an indexer 21 with an arbitrary matrix of n×m rows and columns of outlet channels 22.

Figure 3B:
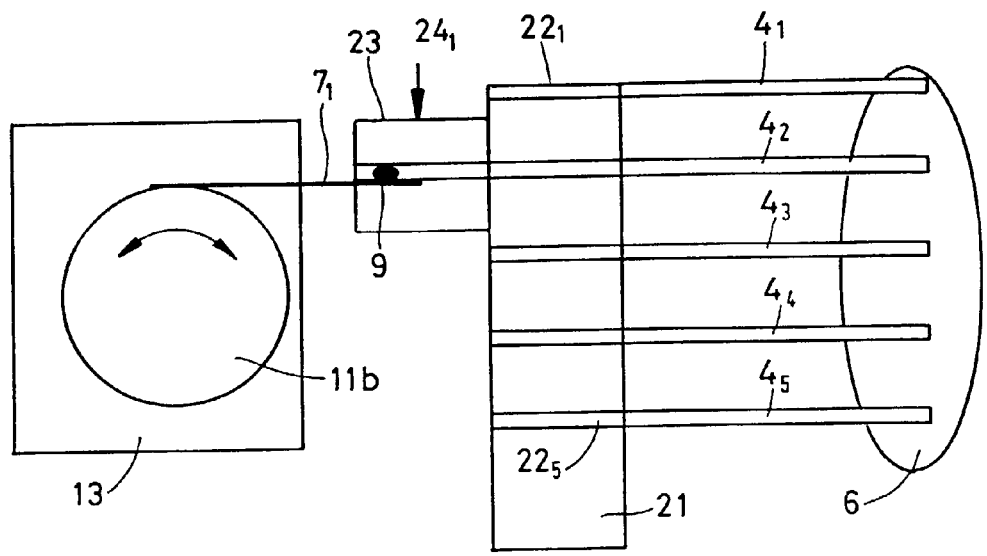

A simplified embodiment of the afterloading device as shown in FIG. 3a is depicted in FIG. 3b, wherein the indexer 21 is provided with five outlet channels $22_1$-$22_5$ arranged in one row and a guide block 23 provided with only one bore $24_1$. With this simplified embodiment only one radiation emitting source $9_1$ can be advanced in a sequential order with the transport wire $7_1$ through one of said five guide tubes $4_1$-$4_5$ towards one of the five different locations in the tumour 6, in order to perform sequentially at each location a preplanned radiation therapy session. The guide block 23, which is brought in alignment with one of the outlet channels $22_1$-$22_5$/guide tubes $4_1$-$4_5$ guides the transport wire $7_1$ and the X-ray emitting source $9_1$ through one of the outlet channel $22_1$-$22_5$ towards the desired location into the tumour 6.

The X-ray emitting source 9 as used in the afterloading device according to the invention, as disclosed in the FIGS. 2a-2b and 3a-3b is powered by suitable high voltage supply means 17, which means 17 are connected with the X-ray emitting source through a suitable supply line 19. Preferably in this embodiments the X-ray emitting source 9 is powered by a voltage in the range of 10 kV to 100 kV. Furthermore each X-ray emitting source 9 is connected to a laser device 16 by means of an optical fibre 18 passing through the transport wire 7 through which optical fibres $18_1$-$18_n$ (in case n X-ray emitting sources $9_n$ are used). Optical light pulses generated by the laser device 16 and propagating towards the X-ray emitting source 9 through the optical fibre are used to create free electrons using the photo-electrical effect, which free electrons are accelerated through for example focussing electrodes towards the anode by means of a voltage difference supplied by said high voltage power supply 17. This voltage difference creates an electrical field for accelerating said electrons.

By using suitable control means the electron beam can be guided and directed using suitable focussing electrodes means known in the art, which accelerated electrons impinge on the anode for creating the desired X-ray beam of a desired intensity and amount, which X-ray beam leaves the X-ray emitting source 9 through an aperture towards the site of intended therapy. The functionality and control of such X-ray emitting source is well known in the art.

Figure 4:
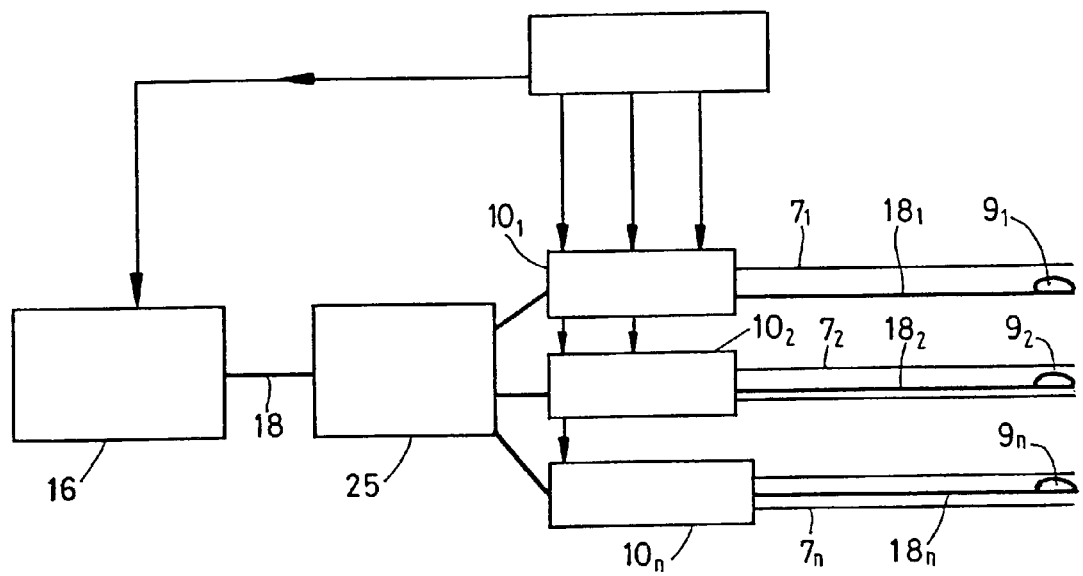
FIG. 4 a further detail of an embodiment of a afterloading device according to the invention.

A simplified construction of an afterloading device using a plurality of X-ray emitting sources is shown in FIG. 4 wherein the optical fibres $18_1$-$18_n$ for n X-ray emitting sources $9_1$-$9_n$ are connected by means of a beam splitter 25 towards one laser device 16. The beam splitter 15 is connected with an optical fibre 18 to the laser device 16 and splits the light pulses emitted by the laser device via n separate optical fibres $18_1$-$18_n$ towards the respective transport wire $7_1$-$7_n$. In this embodiment each transport wire $7_1$-$7_n$ and corresponding X-ray emitting source $9_1$-$9_n$ is advanced by separate transport means $10_1$-$10_n$ for example as disclosed in FIG. 2a. Therefore each X-ray emitting source 9 can be separately positioned independently of the intended position of the other X-ray emitting sources in the tumour 6 to be treated, whilst said X-ray emitting sources are simultaneously activated and driven by the same laser device by means of the beam splitter 25.

Figure 5:
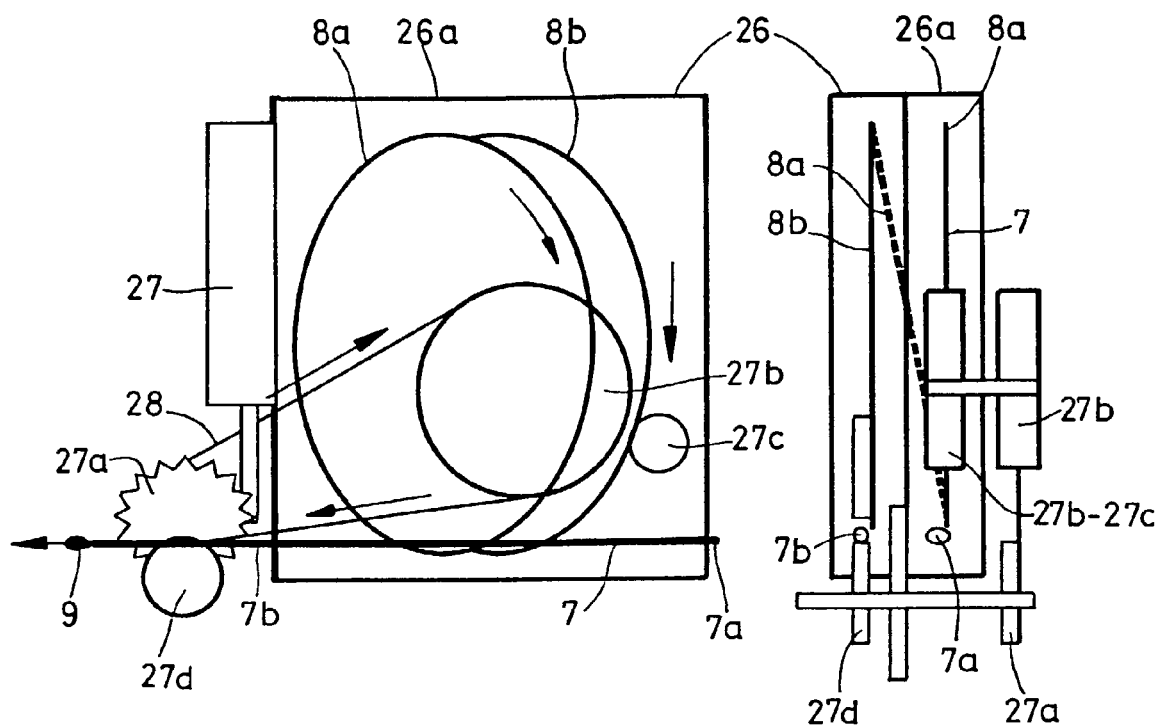
FIG. 5 another further embodiment of transport means for use in an afterloading device according to the invention.
Figure 6:
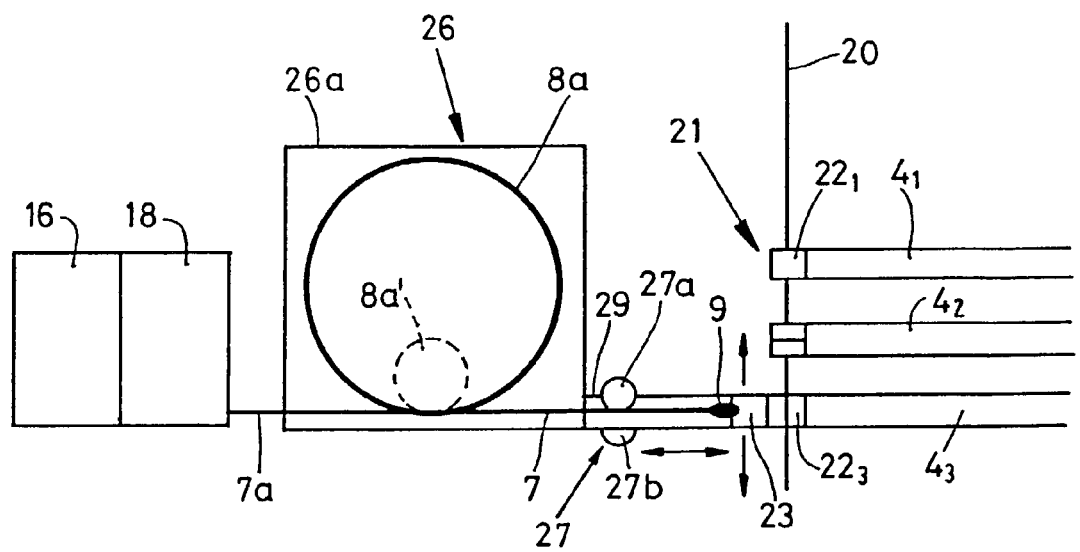
FIG. 6 a further embodiment of transport means combined with indexer means for use in an afterloading device according to the invention.

Another specific embodiment of the transport means 10, is disclosed in the FIGS. 5 and 6, wherein the transport means 26 do not incorporate the drum 11 as disclosed in the FIGS. 2a and 2b, but wherein the transport wire 7 together with the optical fibre 18 and the power supply line 19 are wound in one or more loose windings 8a and 8b into the cartridge 26a of the transport means 26. Transport means 26 comprises also drive means 27, which advance or retract by means of a belt drive 28 a transport wheel 27a, 27b and 27c the transport wire 7 out and in the cartridge 26a thereby moving the X-ray emitting source 9 through the corresponding outlet channel (not shown) and a suitable guide tube 4 (not shown) towards the tumour 6 to be treated.

A similar embodiment of said transport means 26 is depicted in FIG. 6 wherein the transport wire 7 is accommodated in the cartridge 26 with one winding 8a and wherein the laser device and power supply 18 are not integrally combined with the transport means 26 contrary to the embodiments as disclosed in FIGS. 2a-2b. Point 7a of the transport wire 7 can be considered as a fixed point of the wire 7, which wire 7 is advanced in and out the cartridge 26a by means of drive means 27 comprising to drive wheels 27a and 27b which can be brought into contact with the transport wire 7. Suitable encoding means 29 can detect the advanced or retracted length of the transport wire 7 in order to obtain an accurate position of the X-ray emitting source 9 within the guide tube 4 and/or in the tumour 6.

With this embodiment it is easy to establish a correct position of the X-ray emitting source 9 in or near the site of the intended radiation therapy. Also in this embodiment of FIG. 6 indexer 21 contains three outlet channels $22_1$-$22_3$ together with a guide block 23 for guiding the single transport wire 7 together with the X-ray emitting source 9 towards one of the three guide tubes $4_1$-$4_3$.

Although in the description the invention is described by means of embodiments incorporating an X-ray emitting source, which is operative between an activated and an un-activated state, it is noted that these embodiments only serve for illustrating the invention. In fact every electro-magnetic radiation emitting source, which can be switched between an activated and an un-activated state, can be used for the purpose of effecting radiation therapy according to the principles of the invention.

Therefore it is also possible to use the device according to the invention for effecting photodynamic radiation therapy, wherein the radiation emitting source 9 is constructed as the tip of an optical fibre, which flexible fibre is accommodated in the transport wire and which flexible fibre can be moved, twisted and manipulated towards the desired site of intended therapy. The laser device 16 is then used to generate light or light pulses at a very precise wavelength so it can deliver said electro-magnetic radiation to the disease site.

Therefore in the drawings the activatable radiation emitting source 9 can be: 1) an X-ray emitting source activated by a high voltage power supply 17 and optionally by a laser device 16 and 2) the tip of an optical fibre present in the transport wire 7, which optical fibre is connected with its other end with a laser device 16 for effecting photodynamic radiation therapy.

Therefore it should be observed that in this specification electro-magnetic radiation comprises not only X-ray radiation but also electro-magnetic light produced by a laser device.

Moreover due to the fact that the transport wire with the radiation emitting source can be accurately positioned inside an animal body the tip of the optical fibre emitting laser light can also be used for laser-surgery techniques.

When the electro-magnetic radiation emitting source is inserted into one guide tube in the tumour multiple irradiation positions are possible by advancing the source towards different irradiation positions inside the same guide tube.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A device for effecting radiation therapy in an animal body comprising a housing provided with at least:
   one outlet channel;
   a guide tube connected at one end with said outlet channel and wherein the other end of said guide tube is positionable in said animal body near the site of the intended radiation therapy;
   one electromagnetic radiation emitting source connected to a first end of a transport wire, wherein said electromagnetic radiation emitting source is an activatable source operative between an activated and un-activated state using a power supply placed outside the animal body; and
   transport means for moving said transport wire and said radiation emitting source via said outlet channel through said guide tube to and from said site of the intended radiation therapy in said body, wherein:
   said transport wire comprises a power supply line for connecting said activatable radiation emitting source with the power supply; and wherein said transport means comprise a rotatable drum, which is rotationally symmetric around a rotation axis, which drum is provided with two end surfaces and a circumferential surface provided with at least one winding groove for at least one transport wire and wherein said power supply is mounted at an end surface of said drum.

2. The device according to claim 1, wherein said drum is at least partly hollow.

3. The device according to claim 2, wherein said power supply is mounted inside said drum.

4. The device according to claim 1, wherein said power supply is a high voltage power supply.

5. The device according to claim 1, wherein said power supply is connected to a plurality of power supply lines.

6. The device according to claim 1, wherein said power supply line comprises an optical fibre and said power supply comprises a laser device.

7. The device according to claim 6, wherein said laser device is connected to a plurality of optical fibre power supply lines by means of a beam splitter.

8. The device according to claim 1, wherein said device comprises an indexer provided with a plurality of outlet channels to which a plurality of said guide tubes are connected.

9. The device according to claim 8, wherein said indexer is provided with means for directing at least said activatable radiation emitting source through at least one of said plurality of outlet channels.

10. The device according to claim 9, wherein said means comprise a guide block provided with at least one bore, which block is movable connected to the indexer, and wherein said at least one bore can be brought in alignment with at least one of said plurality of outlet channels.

11. The device according to claim 10, wherein said guide block is provided with a row of a plurality of bores, which row can be brought in alignment with a row of a plurality of said outlet channels.

12. The device according to claim 1, wherein said activatable radiation emitting source is an X-ray emitting source.

13. The device according to claim 1, wherein said activatable radiation emitting source is the tip of an optical fibre emitting light contained in said transport wire.

14. The device according to claim 1, wherein in the un-activated state said activatable radiation emitting source is used as a test source for testing the implantation through at least one guide tube towards a site of the intended radiation therapy in said body.

15. A device for effecting radiation therapy in an animal body comprising a housing provided with at least:
- one outlet channel;
- a guide tube connected at one end with said outlet channel and wherein the other end of said guide tube is positionable in said animal body near the site of the intended radiation therapy;
- one electromagnetic radiation emitting source connected to a first end of a transport wire, wherein said electromagnetic radiation emitting source is an activatable source operative between an activated and un-activated state using a power supply placed outside the animal body; and
- transport means for moving said transport wire and said radiation emitting source via said outlet channel through said guide tube to and from said site of the intended radiation therapy in said body, wherein:
- said transport means comprises at least a cartridge having one inlet and one outlet opening for a transport wire, which transport wire is freely accommodated in at least one winding within said cartridge and wherein said transport wire comprises a power supply line for connecting said activatable radiation emitting source with the power supply.

16. The device according to claim 15, wherein said transport wire is fixedly connected to said cartridge near said inlet opening.

17. The device according to claim 15, wherein at least two drivable transport wheels are mounted within said cartridge between which transport wheels said transport wire is guided.

18. The device according to claim 17, wherein drive means are mounted near said outlet opening of said cartridge for driving said transport wheels.

19. The device according to claim 15, wherein said power supply is a high voltage power supply.

20. The device according to claim 15, wherein said power supply is connected to a plurality of power supply lines.

21. The device according to claim 15, wherein said power supply line comprises an optical fibre and said power supply comprises a laser device.

22. The device according to claim 21, wherein said laser device is connected to a plurality of optical fibre power supply lines by means of a beam splitter.

23. The device according to claim 15, wherein said device comprises an indexer provided with a plurality of outlet channels to which a plurality of said guide tubes are connected.

24. The device according to claim 23, wherein said indexer is provided means for directing at least said activatable radiation emitting source through at least one of said plurality of outlet channels.

25. The device according to claim 24, wherein said means comprise a guide block provided with at least one bore, which block is movable connected to the indexer, and wherein said at least one bore can be brought in alignment with at least one of said plurality of outlet channels.

26. The device according to claim 25, wherein said guide block is provided with a row of a plurality of bores, which row can be brought in alignment with a row of a plurality of said outlet channels.

27. The device according to claim 15, wherein said activatable radiation emitting source is an X-ray emitting source.

28. The device according to claim 15, wherein said activatable radiation emitting source is the top of an optical fibre emitting light contained in said transport wire.

29. The device according to claim 15, wherein in the un-activated state said activatable radiation emitting source is used as a test source for testing the implantation through at least one guide tube towards a site of the intended radiation therapy in said body.

30. The device according to claim 18, wherein the transport wheels are driven via a belt transmission.

* * * * *